United States Patent [19]

Falk

[11] Patent Number: 4,778,281

[45] Date of Patent: Oct. 18, 1988

[54] MOLTEN METAL SAMPLER WITH HEAT SENSORS

[76] Inventor: Richard A. Falk, 519 Westminster Dr., Waukesha, Wis. 53186

[21] Appl. No.: 452,537

[22] Filed: Dec. 23, 1982

Related U.S. Application Data

[63] Continuation of Ser. No. 325,167, Nov. 27, 1981, abandoned, which is a continuation of Ser. No. 104,213, Dec. 17, 1979, abandoned, which is a continuation-in-part of Ser. No. 033,637, Apr. 26, 1979, abandoned.

[51] Int. Cl.$^4$ .......................... G01K 7/02; G01K 1/08
[52] U.S. Cl. ................................... 374/140; 374/179; 136/234; 73/DIG. 9
[58] Field of Search .................. 73/354, 359 R, 17 R, 73/341, DIG. 9, 425.4; 136/234, 231, 232, 233, 230; 164/4; 374/26, 157, 139, 140, 179, 181, 182

[56] References Cited

U.S. PATENT DOCUMENTS

| | | | |
|---|---|---|---|
| 3,455,164 | 7/1969 | Boyle | 73/354 |
| 3,463,005 | 8/1969 | Hance | 73/341 |
| 3,481,201 | 12/1969 | Falk | 73/425.4 |
| 3,685,359 | 8/1972 | Boron | 73/354 |
| 3,709,040 | 1/1973 | Coe | 73/354 |
| 3,756,082 | 9/1973 | Bardenheuer | 73/17 R |
| 3,791,219 | 2/1974 | Falk | 73/425.4 R |
| 3,877,309 | 4/1975 | Hance | 73/425.4 R |
| 4,002,069 | 1/1977 | Takemura | 73/354 |
| 4,069,715 | 1/1978 | Falk | 73/425.4 R |

*Primary Examiner*—William A. Cuchlinski, Jr.
*Assistant Examiner*—W. Morris Worth
*Attorney, Agent, or Firm*—Fuller, Puerner & Hohenfeldt

[57] ABSTRACT

A molten metal sampler includes a bath temperature thermocouple and cooling curve thermocouple in the sample cavity. The thermocouple tubes are mounted in a common connector and are in intersecting planes to provide a compact arrangement. The legs of the longer tube are bowed outwardly adjacent the tip of the cooling curve tube to minimize cooling effect on the tip during the cooling curve measurement. In all embodiments, a thermocouple support tube extends through the sample cavity for exposure to the molten metal to measure bath temperature.

3 Claims, 2 Drawing Sheets

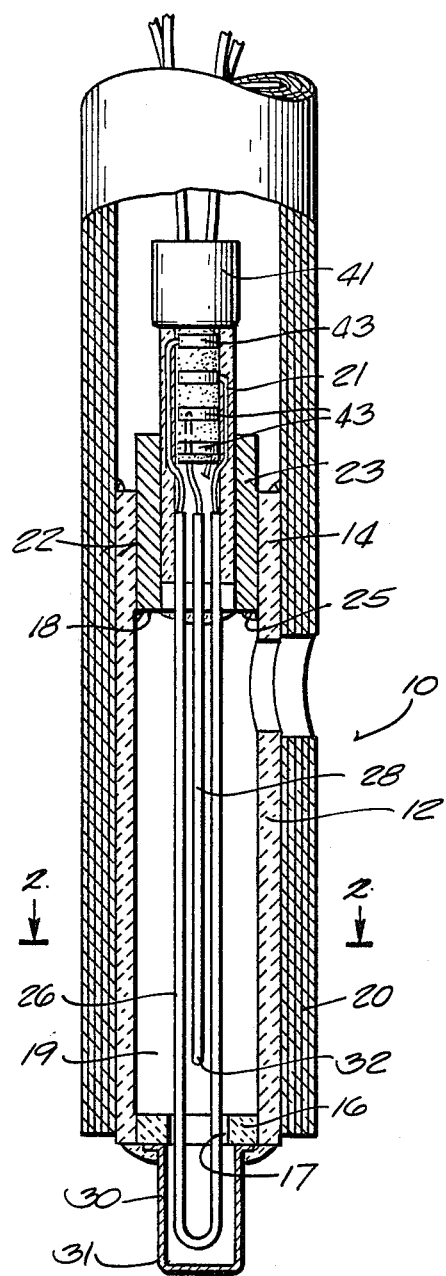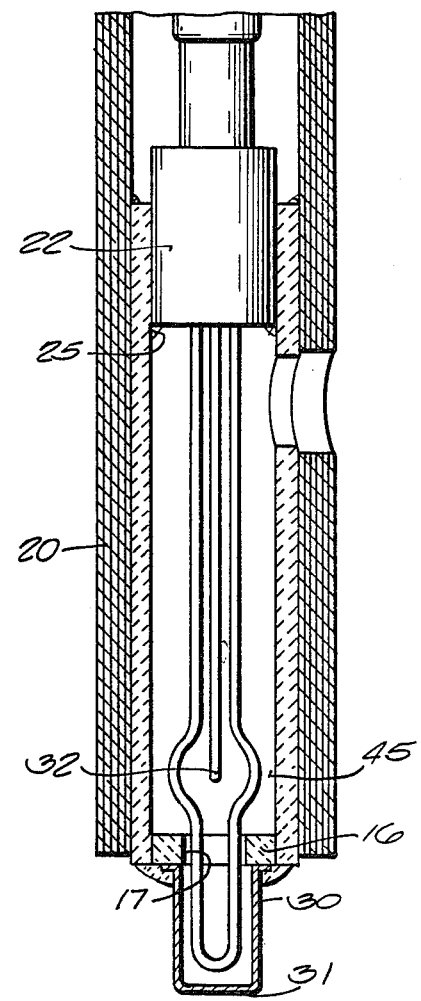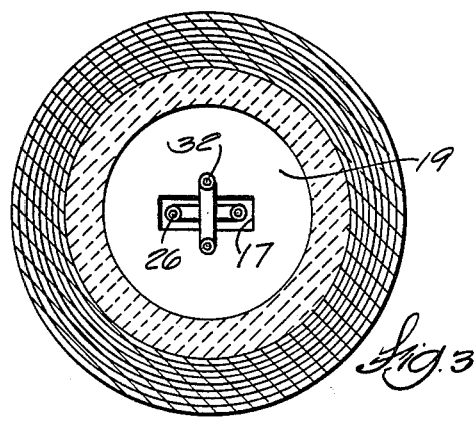

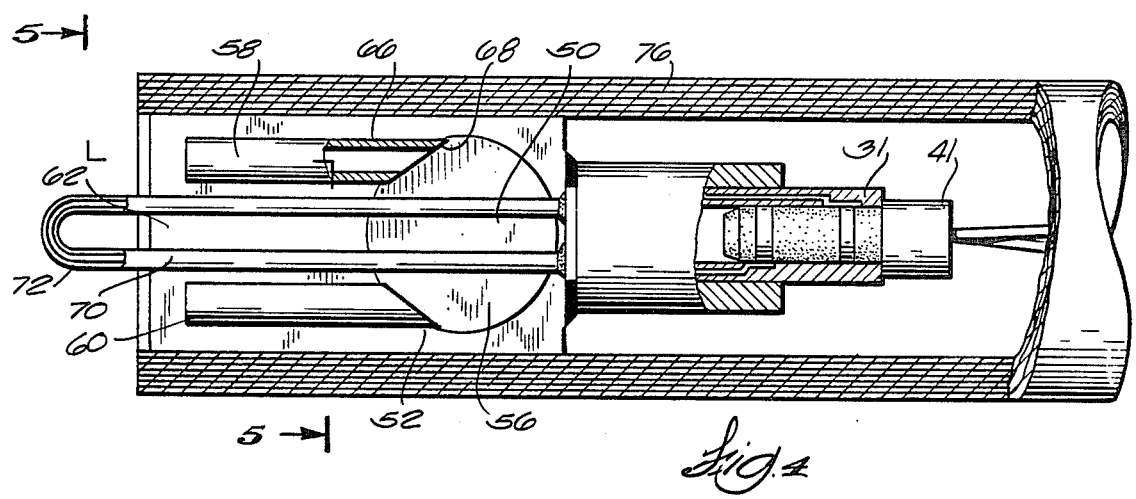
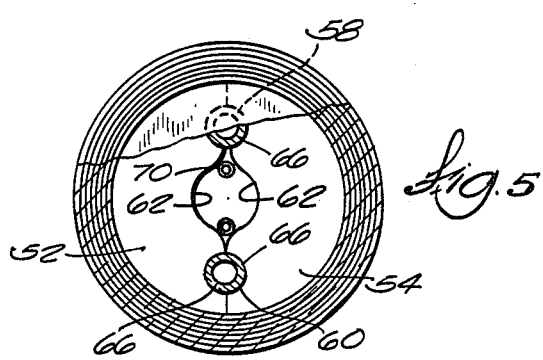
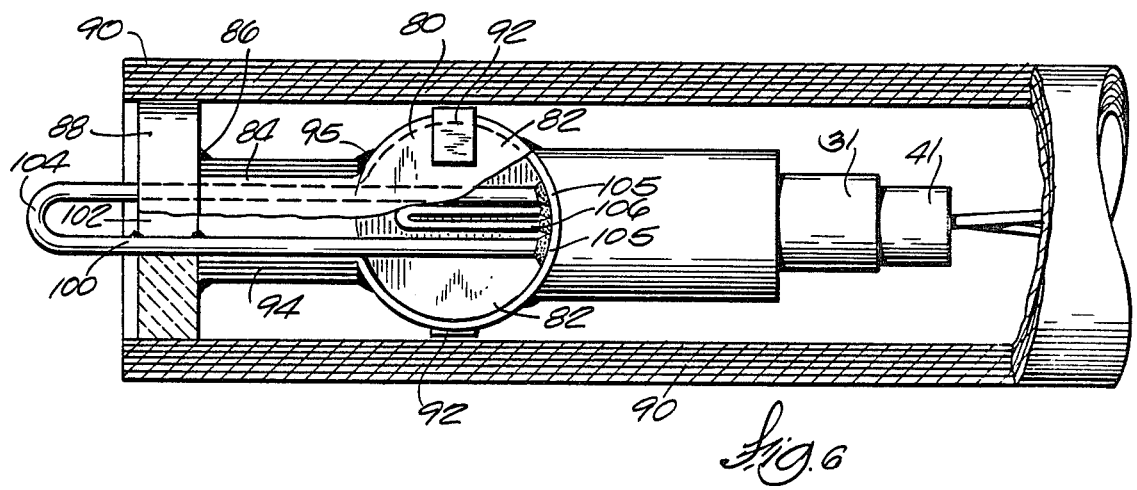

MOLTEN METAL SAMPLER WITH HEAT SENSORS

CROSS REFERENCE TO RELATED APPLICATION

This application is a continuation of application Ser. No. 325,167, filed 11/27/81, now abandoned, which is a continuation of application Ser. No. 104,213, filed 12/17/79 now abandoned, which is a continuation-in-part of application Ser. No. 033,637, filed 4/26/79, now abandoned.

BACKGROUND OF THE INVENTION

The invention relates to a molten metal sampling device which employs two thermocouples, one for sensing bath temperature and the other for determining the liquidus arrest temperature of the sample in the mold cavity. My U.S. Pat. No. 3,481,201 shows the use of thermocouples for taking both bath temperatures and the liquidus arrest temperature of the sample within the sample cavity. Various patents show the use of two thermocouples for simultaneously recording these temperatures. The Boyle U.S. Pat. No. 3,455,164; Hance U.S. Pat. No. 3,463,005; Boron U.S. Pat. No. 3,685,359; and Takamura, et al. U.S. Pat. No. 4,002,069 are illustrative of patents having two thermocouples for dual temperature measurements. These prior art patents require numerous separate parts and time consuming assembly techniques. The present invention provides a relatively simple unitary assembly of two thermocouples which is easily positioned in the sampler.

SUMMARY OF THE INVENTION

The invention provides two thermocouples, one for bath temperature and one for measurement of the cooling curve for determination of the liquidus arrest temperature. Both thermocouples are mounted in a single connector head which includes a jack for receiving an electrical plug. The thermocouple assembly requires a minimum of parts, thus reducing assembly time and overall cost.

More specifically, the thermocouple connector head supports and provides connecting terminals for two fused quartz U-shaped thermocouple tubes which are mounted so that they are nested together. That is, planes through the U-tube legs of each thermocouple are generally at right angles and the sample cooling curve temperature tube, which is shorter, is located within and spaced from the tip of the bath temperature tube. This provides a compact arrangement. To eliminate any cooling effect that the fused quartz legs of the bath temperature thermocouple might have on molten metal adjacent the tip of the cooling curve thermocouple during measurement thereof, the legs of the bath temperature thermocouple are desirably bowed outwardly to space the legs from the tip and junction of the cooling curve thermocouple.

Further objects, advantages and features of the invention will become apparent from the disclosure.

DESCRIPTION OF THE DRAWINGS

FIG. 1 is a side elevational view of a sampler in accordance with the invention.

FIG. 2 is a side elevational view of a modified embodiment of the invention.

FIG. 3 is an enlarged sectional view along line 2—2 of FIG. 1.

FIG. 4 is a fragmentary sectional view of a modified embodiment.

FIG. 5 is a view along line 5—5 of FIG. 4.

FIG. 6 is a fragmentary view of a further modified embodiment.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structure. The scope of the invention is defined in the claims appended hereto.

The sampling lance 10 includes a refractory cartridge 12 with a cylindrical wall 14 and end walls 16 and 18 which define a sample forming cavity 19. End wall 16 has a slot 17 for receiving the bath temperature thermocouple tube as hereinafter described. The cartridge can be contained in a paperboard sleeve 20 as is well known in the art. The thermocouple mounting and connector head 22 comprises several paperboard sleeves. As disclosed, there is an inner sleeve 21 which interfits in an outer paperboard sleeve 23. The outer paperboard sleeve projects through opening 25 in end wall 18 and is secured in place by refractory cement.

The thermocouple connector head 22 includes a first fused quartz tube 26 and a second tube 28. The first tube 26 is longer than the second tube and projects through the slot for exposure to the bath upon immersion of the sampler. A protective fusible cap 31 protects the tip 33. The tube 26 is fused quartz and U-shaped as is typical in the art and has its ends anchored in the head 22. The second tube 28 is also U-shaped and is shorter in length and has its tip 32 located between the opposed runs or legs 34 and 36 of the first tube 26. The tubes 26, 28 are nested together to provide a compact, easily assembled construction. Moreover, the outer tube 26 provides some protection for the inner tube 28 during and prior to assembly. The leads for the thermocouples are contained in the cardboard sleeves and exposed in the interior 37 of sleeve 21 for electrical connection with a plug 41. As disclosed, the plug has four band conductors 43 for electrical connection with the exposed thermocouple leads.

As best shown in FIG. 2, the legs of U-tube 26 are desirably bowed or spaced outwardly at 45 to minimize the cooling effect of the legs of tube 26 adjacent the tip 32.

FIGS. 4, 5 and 6 show further modified embodiments. In FIGS. 4 and 5 the sample cavity 50 is defined by refractory mold halves 52, 54 (FIG. 5) which have recesses 56, 58, 60 and 62. The recesses 56 cooperate to provide a cylindrical disc-shaped mold cavity, and the passages 58 and 60 in each mold half receive and support pin sample tubes 66 which communicate at 68 with the mold cavity 50. Recesses 62 provide a fill passage to the sample cavity 50.

A fused quartz thermocouple tube 70 extends through the recesses 62 to the sample cavity so that the tip 72 is exposed to measure bath temperature. A sleeve 31 and plug 41, as described above, are provided to make the electrical connection. The components described in FIGS. 4 and 5 are housed in a paperboard sleeve 76.

In FIG. 6 the sample cavity 80 is defined by a pair of metal mold halves 82 which have metal neck portions 84 which are cemented by refractory cement 86 to a refractory disc 88. The refractory disc 88 is wedged inside a cardboard sleeve 90 which supports the components. The mold halves are held together by metal clips 92. A cardboard sleeve 94 is cemented to the parts by a refractory cement bead 86 and a bead of refractory cement 95.

In accordance with the invention, a fused quartz U-shaped thermocouple tube 100 extends through the mold cavity and the neck portions 84 and through the aperture 102 in the ceramic disc to expose the tip 104 to the bath. Notches 105 in the mold halves enable insertion of the tube 100 past the wall of the mold halves. A cooling curved thermocouple 106 can also extend into the mold cavity. A connecting sleeve 31 and electrical plug 41 can be employed for the electrical connections.

Although the drawings show U-shaped protective tubes for the thermocouple leads and elements, a single tube containing isolated leads and the thermocouple junction can be employed to obtain the advantages of the invention.

What is claimed is:

1. A molten metal sampler including wall means defining a sample cavity, a side entry fill port for said cavity, heat sensing means for measuring molten metal bath temperature and the liquidus arrest temperature, said heat sensing means including a bath temperature thermocouple element and a liquidus arrest temperature thermocouple element, first and second elongated U-shaped protective tubes for said elements, and connecting and mounting means for said tubes for supporting said tubes in said cavity with said tip of said first tube located within said cavity and said tip of said second tube extending through a slot and located outside of said cavity, with said first and second U-tubes nested together in intersecting planes, with said first tip located within a plane extending through the legs of said second tube.

2. The sampler of claim 1 wherein said legs of said second tube are bowed outwardly adjacent the tip of said first tube to minimize cooling of molten metal adjacent said tip of said first tube.

3. The sampler of claim 1 wherein said legs of said second tube are spaced outwardly adjacent the tip of said first tube.

* * * * *